United States Patent
Wierson

Patent Number: 5,707,645
Date of Patent: Jan. 13, 1998

[54] HEMORRHOIDAL ICE-TREATMENT DEVICE

[76] Inventor: Mark Wierson, 9871 N. Banditt Trail, Tucson, Ariz. 85742

[21] Appl. No.: 711,545

[22] Filed: Sep. 10, 1996

Related U.S. Application Data

[60] Continuation-in-part of provisional application No. 60/003,529 Sep. 11, 1995.

[51] Int. Cl.⁶ .................................................. A61F 7/12
[52] U.S. Cl. ..................... 424/436; 514/882; 514/953; 514/966; 607/108; 607/113; 604/113
[58] Field of Search ......................... 424/436; 514/882, 514/953, 966; 607/108, 113; 604/113

[56] References Cited

U.S. PATENT DOCUMENTS

| | | |
|---|---|---|
| 3,809,096 | 5/1974 | York .................................. 607/424 |
| 4,240,436 | 12/1980 | Singleton ........................... 607/108 |
| 4,563,182 | 1/1986 | Stoy et al. ......................... 607/113 |
| 4,844,073 | 7/1989 | Pohler ............................... 607/113 |
| 4,932,397 | 6/1990 | McFaul, Sr. . |
| 4,938,221 | 7/1990 | Tuffel ............................... 607/113 |
| 5,062,425 | 11/1991 | Tucker .............................. 604/97 |
| 5,192,266 | 3/1993 | Wilk . |
| 5,263,926 | 11/1993 | Wilk . |

*Primary Examiner*—Amy Hulina
*Attorney, Agent, or Firm*—Antonio R. Durando

[57] ABSTRACT

A small, reusable, previously cooled or frozen bladder that is applied to the anal area of a user. The bladder consists of two two-ply sheets of a flexible, semi-porous material, such as polyethylene, hermetically heat sealed together at the edges to form an internal cavity. The cavity contains a cold-temperature storage means, such as water, glycerol, a combination thereof, or other chemical slurry, and a medicinal agent, such as witchhazel, shark oil, yarrow, other astringents, and lidocaine or other pain relievers.

17 Claims, 2 Drawing Sheets

5,707,645

HEMORRHOIDAL ICE-TREATMENT DEVICE

RELATED APPLICATIONS

This application is a continuation-in-part of United States Provisional Patent Application Serial Number 60/003,529, filed by the same inventor on Sep. 11, 1995, entitled "Method and Device for the Treatment of Hemorrhoids and Other Diseases and Injuries to the Perineal Area of the Human Body."

BACKGROUND OF THE INVENTION

1. Field of the Invention

This invention pertains to the general field of methods and devices for treating ailments with ice packs. In particular, it concerns a novel device for providing ice treatment and medication for hemorrhoids in a patient.

2. Description of the Prior Art

Hemorrhoids are painful swellings or tumors of a vein in the region of the anus that cause pain, itching, bleeding, and general discomfort. Many products and therapies for the treatment of hemorrhoids exist, including salves, ointments, solution-impregnated pads, the application of heat, and various surgical procedures.

Most of the available over-the-counter preparations contain an analgesic component, a lubricant to ease the strain and pressure associated with bowel movements, and/or a topical steroid in low concentration. These preparations provide only temporary relief from hemorrhoidal discomfort, and they do not induce a significant reduction in swelling or edema, or reduce any of the other actual causes of the pain. Prescription preparations generally contain the same types of ingredients as the over the counter products, merely in stronger concentrations.

The application of heat to hemorrhoids may actually exacerbate the condition by inducing increased swelling and edema. Long recognized to promote healing of injured or diseased body parts, the application of heat increases blood flow by vasodilation, and thereby increases the exposure of the injured or diseased areas to blood-born defense mechanisms and repair factors. However, there is now evidence which indicates that exposure of hemorrhoids to heat too early in the injury or disease process increases swelling and may induce thrombosis (strangulated blood clots), which cause intense pain and usually require surgical removal.

Thus, surgery is the most effective method for dealing with hemorrhoids. Surgery is also the most painful, expensive, and unappealing alternative for most individuals and is generally the last treatment mode sought by hemorrhoid sufferers. In addition, surgical removal of hemorrhoids normally creates painful episiotomy wounds.

Although the application of cold to hemorrhoids is not novel, such applications are normally reserved for the post-surgical period for control of additional swelling, especially in episiotomy wounds, and to ease pain resulting from the surgical process. These applications typically embody an oblong disposable rectal insert (Pohler, U.S. Pat. No. 4,844,073; Tuffel, U.S. Pat. No. 4,938,221; and Tucker, U.S. Pat. No. 5,062,425) or pad (York, U.S. Pat. No. 3,809,096; and Singleton, U.S. Pat. No. 4,240,436) containing water or another thermal storage means. None of the known devices is suitable for external use in treating hemorrhoids and none includes means for dispensing medication to the injured area. Therefore, there is still a need for an anal or perineal ice pack of general external use that provides both cold and medication treatment to a user.

BRIEF SUMMARY OF THE INVENTION

It is therefore an objective of this invention to provide a cold-pack device of general external use for alleviating hemorrhoidal symptoms.

Another object of the invention is a cold pack that incorporates medication for gradual release over the anal surface of a user.

Another objective of the invention is a device that can be frozen and reused periodically over extended periods of time.

Yet another goal of the invention is a device that is easy to use and does not require immobilization of a patient.

Finally, an objective of the invention is a device that is inexpensive and easily manufactured with existing materials and components.

In accordance with these and other objectives, this invention relates to a therapeutic cold bladder and its application for the relief of hemorrhoidal discomfort. The device consists of a small, reusable, previously cooled or frozen bladder applied to the anal or perineal area of a user. The bladder consists of two two-ply sheets of a flexible, semiporous material, such as polyethylene, hermetically heat sealed together at the edges to form an internal cavity. The cavity contains a cold-temperature storage means, such as water, glycerol, a combination thereof, or other chemical slurry, and a medicinal agent, such as witchhazel, shark oil, yarrow, other astringents, and lidocaine or other pain relievers.

Various other purposes and advantages of the invention will become clear from its description in the specification that follows, and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose only some of the various ways in which the invention may be practiced.

DETAILED DESCRIPTION OF THE INVENTION

The invention discloses a device for the topical application of cold, with or without additional medications, to external hemorrhoids for both general, day-to-day alleviation of hemorrhoid discomfort and long-term reduction of hemorrhoid swelling and edema, the underlying causes of hemorrhoid discomfort. In trial day-to-day use of this device at the first sensation of hemorrhoid discomfort, this invention was observed to often abort the attack, delay recurrence for weeks, and shorten the duration of the remaining attacks.

For the purposes of this disclosure, a semi-porous or semi-permeable material is defined as a material having no measurable permeability to liquids in general, and to water or water solutions in particular, at room temperature and atmospheric pressure, but exhibiting some degree of permeability as the pressure and temperature are increased. Specifically, a material that prevents leakage under normal conditions but allows seepage at a rate no greater than 1 ml per hour per 100 cm$^2$ of surface when subjected to a pressure drop of about 0.5 atmospheres is considered semi-permeable.

Figure 1:
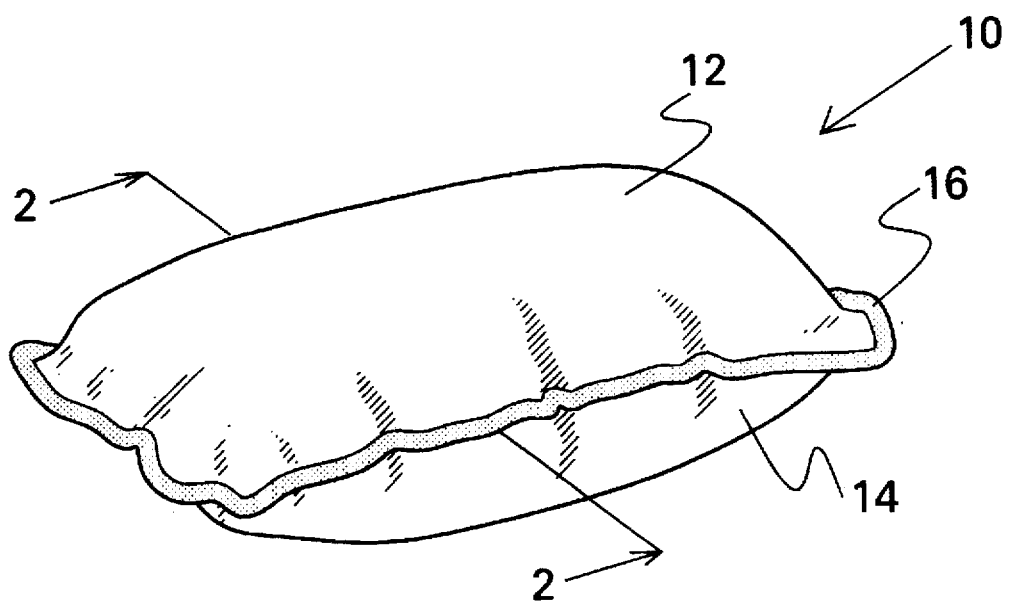
FIG. 1 is a perspective view of a cold-pack bladder according to the preferred embodiment of the invention.
Figure 4:
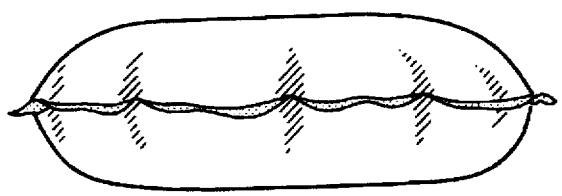
FIGS. 4 and 5 are elevational front and side views, respectively, of the cold-pack bladder of FIG. 1.
Figure 5:
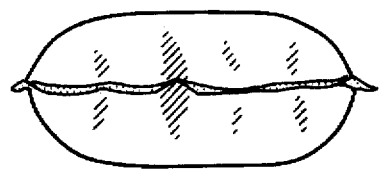
Figure 6:
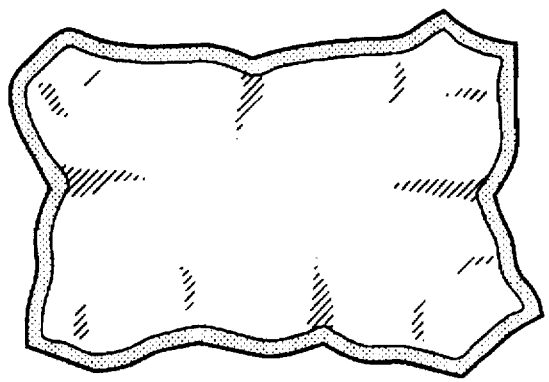
FIG. 6 is a top view of the cold-pack bladder of FIG. 1.
Figure 2:
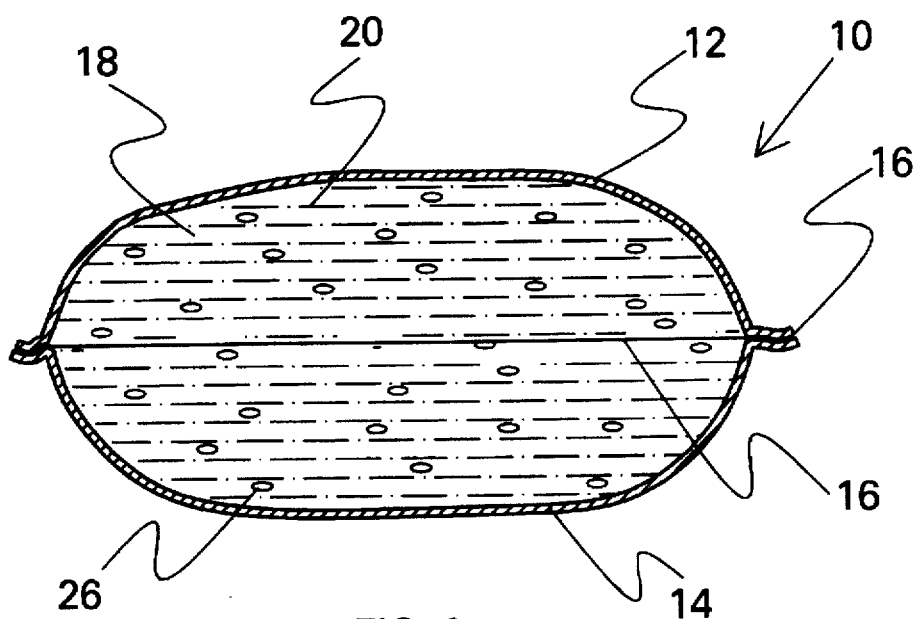
FIG. 2 is a schematic cross-sectional view taken from line 2—2 in FIG. 1, wherein the thickness of the wall material is exaggerated to illustrate the separate components of the bladder.

Referring to the drawings, wherein the same reference numbers and symbols are used throughout to designate like parts, FIG. 1 is a perspective view of the preferred embodiment of a cold-pack bag or bladder 10 according to the invention. The bladder consists of a substantially symmetric structure in the shape of a pillow. The bladder 10 is a single-seamed, hermetically sealed bag formed from two sheets of polyethylene film, chosen for its relatively low cost, flexibility, and substantial non-permeability to liquids under normal temperature and pressure conditions. As seen more particularly in the sectional view of FIG. 2, where the thickness of the material is disproportionately enlarged to illustrate the various parts forming the bladder, a top sheet 12 is joined with a bottom sheet 14 of material through a continuous seam 16 to form an enclosed cavity 18. Prior to completion of the seal along the seam 16, the cavity 18 is filled with a congealable liquid 20, such that the bladder 10 can be advantageously frozen and utilized as a cold pack.

The device is constructed using conventional manufacturing techniques and equipment. In one embodiment of the invention, the bladder 10 is formed by introducing a sufficient amount of liquid 20 (such as to form a layer about 0.75 to 1.00 inch thick) over the bottom sheet 14 of polyethylene film, and then covering the liquid with the top sheet 12 of polyethylene film. A heated seal-cut device is applied from both the bottom and the top aspects of the respective polyethylene film sheets, which heat seals the opposing sheets of polyethylene film through the liquid 20, leaving the interior cavity 18 filled with the liquid, and cuts the seam waste at the specified margin as shown in the drawings.

The preferred size of the device is about one and one half to two inches (3.8–5.0 cm) in length, one and one half to two inches (3.8–5.0 cm) in width, and three quarters to one inch (1.8–2.5 cm) in thickness at the midline. This size approximates the normal anal area of most humans.

I found that polyethylene film in a thickness of about 5 thousands of an inch provided the strength necessary for repeated thawing and freezing, while still allowing the pliability required for maximum efficacy of application. In its simplest embodiment, the interior cavity 18 of the bladder 10 was filled with purified water with a trace of chlorine to control harmful bacteria; equivalent results were obtained with carboxymethylcellulose in a suspension of purified water with a trace of chlorine, and with FDA-approved propylene glycol in a suspension of purified drinking water.

The resulting liquid-filled bag has a peripheral single seam 16 with a compression resistance of approximately 25 to 35 psi (as tested in non-frozen conditions at 2 to 8 degrees Celsius on a Chatillon Model HTC compression tester). Similar bags were tested for resistance to low temperature freezing at zero degrees Celsius for 24 hours and then transferred to minus one hundred twenty degrees Celsius for 24 additional hours with no adverse effects following thawing. Similar bags were also tested at −120° C. for 325 hours with no adverse effects following thawing. The shelf-life of the bag at room temperature was tested for two years without appreciable deterioration. It is expected that refrigerated or freezer conditions would extend the shelf-life by many years.

In the preferred embodiment of the invention, instead of a single-ply polyethylene, two layers of material (a thinner clear film inside and a thicker opaque film outside, about 1 and 5 mils thick, respectively) were used for each of the top and bottom walls of the bladder 10. Thus, as illustrated in the sectional view of FIG. 3, two additional sheets of material, 22 and 24, were utilized in forming the cavity 18, thereby further ensuring the integrity of the bladder 30 when subjected to shock and sharp pressure and/or temperature changes. The seam 16 can be formed by heat sealing according to the same process described above for single-ply applications.

In trial uses of this device, the volume of liquid contained within the interior cavity was observed to decreased over time, although no visible sweating or leakage of the trial devices was observed. This occurred with both the single-ply and the two-ply embodiments, thereby indicating some degree of permeability of polyethylene to liquids. It is believed that the increase in both heat and pressure created when the device is utilized perineally or in contact with the anus of a user causes a slight increase in the permeability of the polyethylene sheets, and therefore some seepage and a decrease over time in the volume of liquid contained within the interior cavity of the device. Therefore, this property is exploited in the preferred embodiment of the invention by adding one or more medicinal agents 26, such as witchhazel, shark oil, yarrow, other astringents, and lidocaine or other pain relievers, to the liquid 20 contained in the interior cavity 18 of the bladder 10 of the invention. I found that these medicinal agents slowly diffuse out of the bladder upon perineal or anal use and provide important additional relief from hemorrhoidal discomfort.

Figure 3:
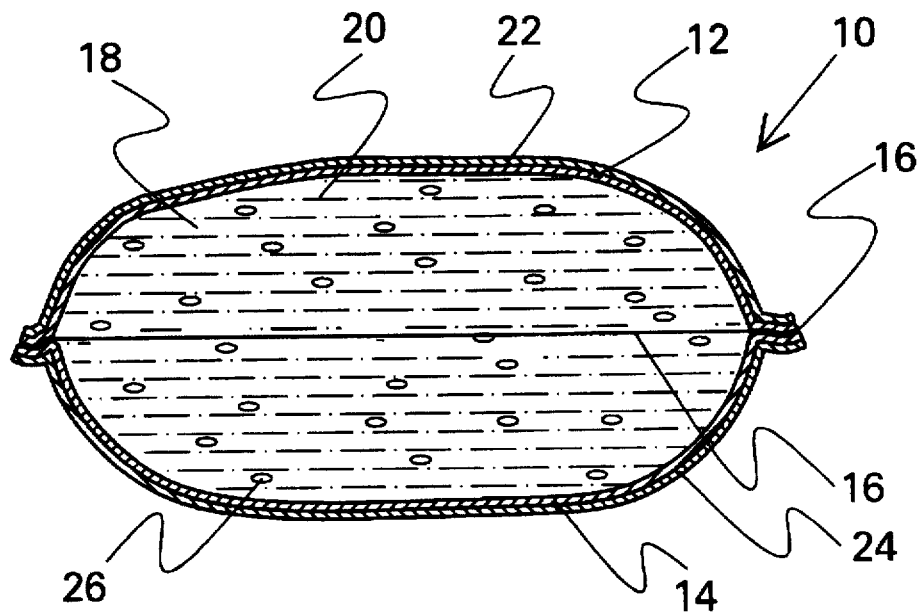
FIG. 3 is a schematic cross-section corresponding to the view of FIG. 2 showing an embodiment of the invention with two-ply walls.

Thus, the preferred embodiment of the invention is based on the use of material that is semi-permeable, as defined above; that is, slightly permeable to a liquid solution containing medication for hemorrhoids, such that the liquid is slowly released during use but in quantities insufficient to materially deplete the bladder, so that the device can be refrozen and used effectively again. I found that the efficacy of the medication is acceptable and retained over time if incorporated into the bladder and used in concentrations substantially equal to those recommended for topical application. For instance, a four-ply bladder as shown in FIG. 3 containing such a water solution of witchhazel was used very effectively at approximately monthly intervals over a period of about 18 months. The liquid volume in the bladder decreased noticeably after that time, but it was still sufficient to provide relief after repeated freeze and reuse cycles.

Thus, the bladder of the invention is intended for medical purposes and is designed to apply cold as well as medication for symptomatic therapy directly to hemorrhoids and/or wounds resulting from episiotomy. When frozen and applied externally for periods of about twenty minutes, it provides fast, temporary, and natural relief from pain, and reduction of swelling, edema, and inflammation of tissues associated with hemorrhoids and episiotomy. The device is not intended for insertion into a body orifice.

The structure of the bladder may include an orifice with a cap, plug, seal, or other closing device. As known to those skilled in the art, alternative methods of manufacture of the bladders 10,30 of the invention could be by preforming with cold temperature moldings; by single-die construction; by opposing-film sheet construction; blow-mold construction; or by two-stage bag construction (where the bladder is formed leaving an opening for insertion of the liquid; then filled and sealed in a secondary operation). Alternative seam sealing technologies are also available, such as radio frequency sealing processes.

The preferred bladder material is polyethylene sheet, but it is expected that rubber, plastic, and other semi-permeable synthetic or natural materials having low permeability to water and water solutions would be suitable to practice the invention. The thickness of the polyethylene sheets in the preferred embodiment was chosen to maximize the flexibility and durability of the device, while retaining the permeability characteristics required for very slow depletion of the inner liquid.

It is understood that variations, adaptations, modifications, or arrangements of or to this device may be instituted by persons skilled in the art. Accordingly, it is not the intention of the inventor to limit the scope of the invention to what has been exactly shown, described, drawn, or presented, but to include within the scope of this application all variations, adaptations, modifications, and arrangements of or to the device.

I claim:

1. A device for the symptomatic treatment of hemorrhoidal discomfort, comprising:
   (a) a bladder having opposite walls defining an enclosed inner cavity, said walls consisting of a semi-permeable material; and
   (b) a congealable liquid contained in said cavity and comprising a medicinal ingredient.

2. The device of claim 1, wherein said material consists of polyethylene.

3. The device of claim 1, wherein said material consists of a two-ply sheet of polyethylene.

4. The device of claim 1, wherein said liquid is water or an aqueous solution.

5. The device of claim 1, wherein said medicinal ingredient is selected from the group consisting of witchhazel, shark oil, yarrow, lidocaine, or mixtures thereof.

6. The device of claim 2, wherein said liquid is water or an aqueous solution.

7. The device of claim 3, wherein said liquid is water or an aqueous solution.

8. The device of claim 2, wherein said medicinal ingredient is selected from the group consisting of witchhazel, shark oil, yarrow, lidocaine, or mixtures thereof.

9. The device of claim 3, wherein said medicinal ingredient is selected from the group consisting of witchhazel, shark oil, yarrow, lidocaine, or mixtures thereof.

10. The device of claim 4, wherein said medicinal ingredient is selected from the group consisting of witchhazel, shark oil, yarrow, lidocaine, or mixtures thereof.

11. The device of claim 6, wherein said medicinal ingredient is selected from the group consisting of witchhazel, shark oil, yarrow, lidocaine, or mixtures thereof.

12. The device of claim 7, wherein said medicinal ingredient is selected from the group consisting of witchhazel, shark oil, yarrow, lidocaine, or mixtures thereof.

13. A method for treating the symptoms of hemorrhoidal discomfort, comprising the following steps:
    (a) providing a bladder having opposite walls defining an enclosed inner cavity, said walls consisting of a semi-permeable material;
    (b) filling said cavity with a congealable liquid comprising a medicinal ingredient and sealing the cavity;
    (c) freezing the liquid to produce a cold-pack device; and
    (d) placing the device within an anal area of a user; thereby providing a cold treatment and concurrently applying said medicinal ingredient to the anal area as the medicinal ingredient is released through the walls of the bladder.

14. The method of claim 13, wherein said material consists of polyethylene.

15. The method of claim 13, wherein said liquid is water or an aqueous solution.

16. The method of claim 13, wherein said medicinal ingredient is selected from the group consisting of witchhazel, shark oil, yarrow, lidocaine, or mixtures thereof.

17. The method of claim 13, wherein said material consists of polyethylene, said liquid is water or an aqueous solution, and said medicinal ingredient is selected from the group consisting of witchhazel, shark oil, yarrow, lidocaine, or mixtures thereof.

* * * * *